United States Patent
Farmer et al.

(10) Patent No.: US 11,758,924 B2
(45) Date of Patent: *Sep. 19, 2023

(54) PASTURE TREATMENTS FOR ENHANCED CARBON SEQUESTRATION AND REDUCTION IN LIVESTOCK-PRODUCED GREENHOUSE GAS EMISSIONS

(71) Applicant: Locus Solutions IPCo, LLC, Solon, OH (US)

(72) Inventors: Sean Farmer, North Miami Beach, FL (US); Ken Alibek, Solon, OH (US)

(73) Assignee: LOCUS SOLUTIONS IPCO, LLC, Solon, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/652,608

(22) PCT Filed: Mar. 30, 2020

(86) PCT No.: PCT/US2020/025754
§ 371 (c)(1),
(2) Date: Mar. 31, 2020

(87) PCT Pub. No.: WO2020/210074
PCT Pub. Date: Oct. 15, 2020

(65) Prior Publication Data
US 2022/0015390 A1    Jan. 20, 2022

Related U.S. Application Data

(60) Provisional application No. 62/967,907, filed on Jan. 30, 2020, provisional application No. 62/885,876, filed on Aug. 13, 2019, provisional application No. 62/833,355, filed on Apr. 12, 2019.

(51) Int. Cl.
| | | |
|---|---|---|
| A23K 10/18 | (2016.01) | |
| A23K 20/147 | (2016.01) | |
| A23K 20/158 | (2016.01) | |
| A23K 20/189 | (2016.01) | |
| A23K 20/20 | (2016.01) | |
| A23K 50/10 | (2016.01) | |
| A23K 10/14 | (2016.01) | |
| C12R 1/85 | (2006.01) | |
| C12R 1/07 | (2006.01) | |

(52) U.S. Cl.
CPC .............. *A23K 10/18* (2016.05); *A23K 10/14* (2016.05); *A23K 20/147* (2016.05); *A23K 20/158* (2016.05); *A23K 20/189* (2016.05); *A23K 20/20* (2016.05); *A23K 50/10* (2016.05); *C12R 2001/07* (2021.05); *C12R 2001/85* (2021.05)

(58) Field of Classification Search
None
See application file for complete search history.

(56) References Cited

U.S. PATENT DOCUMENTS

| | | |
|---|---|---|
| 5,945,333 A | 8/1999 | Rehberger |
| 6,512,166 B1 | 1/2003 | Harman et al. |
| 6,638,910 B2 | 10/2003 | Heins et al. |
| 2003/0228402 A1 | 12/2003 | Franklin et al. |
| 2005/0266036 A1 | 12/2005 | Awada et al. |
| 2006/0057118 A1* | 3/2006 | Toride .................... A23K 10/18 424/93.4 |
| 2009/0285931 A1 | 11/2009 | Shelby et al. |
| 2010/0074872 A1 | 3/2010 | Blaser et al. |
| 2010/0143316 A1 | 6/2010 | Hsieh et al. |
| 2010/0254957 A1 | 10/2010 | Hua |
| 2010/0267684 A1 | 10/2010 | Seong et al. |
| 2011/0033436 A1 | 2/2011 | Chen et al. |
| 2011/0237531 A1 | 9/2011 | Yanagisawa et al. |
| 2011/0274673 A1 | 11/2011 | Kang et al. |
| 2012/0039853 A1 | 2/2012 | Corveleyn et al. |
| 2012/0142621 A1 | 6/2012 | Falus et al. |
| 2012/0207912 A1 | 8/2012 | Nichols et al. |
| 2012/0220464 A1 | 8/2012 | Giessler-Blank et al. |
| 2012/0321592 A1 | 12/2012 | Schmidt et al. |
| 2013/0011384 A1 | 1/2013 | Morgavi et al. |
| 2013/0064927 A1 | 3/2013 | Davis et al. |
| 2013/0205849 A1 | 8/2013 | Kloepper et al. |
| 2013/0324406 A1 | 12/2013 | Chisholm et al. |
| 2014/0112889 A1 | 4/2014 | Berger et al. |
| 2015/0037302 A1 | 2/2015 | Bralkowski et al. |
| 2015/0044356 A1 | 2/2015 | Bootsma et al. |
| 2015/0045290 A1 | 2/2015 | Coutte et al. |
| 2015/0094273 A1 | 4/2015 | Prabhune et al. |
| 2015/0118203 A1 | 4/2015 | Boyette et al. |
| 2015/0297642 A1 | 10/2015 | Borody |

(Continued)

FOREIGN PATENT DOCUMENTS

| | | |
|---|---|---|
| CN | 101528050 A | 9/2009 |
| CN | 103820366 A | 5/2014 |

(Continued)

OTHER PUBLICATIONS

Chung, Y-H., et al., "Differing effects of 2 active dried yeast (*Saccharomyces cerevisiae*) strains on ruminal acidosis and methane production in nonlactating dairy cows", Journal of Dairy Science, vol. 94, No. 5, pp. 2431-2439. (Year: 2011).*

(Continued)

*Primary Examiner* — Michelle F. Paguio Frising
*Assistant Examiner* — Grant C Currens
(74) *Attorney, Agent, or Firm* — SALIWANCHIK, LLOYD & EISENSCHENK

(57) ABSTRACT

The subject invention provides compositions and methods for reducing deleterious atmospheric gases and/or precursors thereof using livestock feed additives and/or supplements. In preferred embodiments, a multi-purpose composition comprising one or more beneficial microorganisms and/or one or more microbial growth by-products is applied to livestock animals' feed and/or to a field or pasture where livestock animals graze. In some embodiments, the composition controls methanogenic bacteria. In some embodiments, the composition enhances carbon sequestration in the field or pasture by promoting plant health and/or growth.

13 Claims, 2 Drawing Sheets

(56) References Cited

U.S. PATENT DOCUMENTS

| | | |
|---|---|---|
| 2016/0040119 A1 | 2/2016 | Hashman |
| 2016/0058804 A1 | 3/2016 | Jones et al. |
| 2016/0073642 A1 | 3/2016 | Ceballos Rojas et al. |
| 2016/0083757 A1 | 3/2016 | Fonseca et al. |
| 2016/0089407 A1 | 3/2016 | Vuorenmaa et al. |
| 2016/0145660 A1 | 5/2016 | Garcia et al. |
| 2016/0152525 A1 | 6/2016 | Chelle et al. |
| 2016/0183556 A1 | 6/2016 | Lu et al. |
| 2016/0374364 A1 | 12/2016 | Lee |
| 2017/0044632 A1 | 2/2017 | Anderson et al. |
| 2017/0196812 A1 | 7/2017 | Belcher et al. |
| 2017/0223956 A1 | 8/2017 | Habib et al. |
| 2017/0224745 A1 | 8/2017 | Dart |

FOREIGN PATENT DOCUMENTS

| | | | | |
|---|---|---|---|---|
| CN | 105087383 | A | 11/2015 | |
| CN | 106045772 | A | 10/2016 | |
| EP | 0540074 | A1 | 5/1993 | |
| KR | 20140019992 | A | 2/2014 | |
| WO | 9525163 | A1 | 9/1995 | |
| WO | 9716974 | A1 | 5/1997 | |
| WO | 2007072848 | A1 | 6/2007 | |
| WO | 2011153299 | A2 | 12/2011 | |
| WO | 2011153299 | A3 | 12/2011 | |
| WO | 2016063305 | A2 | 4/2016 | |
| WO | 2017035101 | A1 | 3/2017 | |
| WO | 2017129576 | A1 | 8/2017 | |
| WO | 2017149266 | A1 | 9/2017 | |
| WO | WO-2017187433 | A1 * | 11/2017 | ............. A23K 10/18 |
| WO | 2018-049182 | A2 | 3/2018 | |

OTHER PUBLICATIONS

Van Kessel et al., "The effect of pH on ruminal methanogenesis", FEMS Microbiology Ecology, vol. 20, pp. 205-210. (Year: 1996).*

Gottlieb et al., "Review article: inhibition of methanogenic archaea by statins as a targeted management strategy for constipation and related disorders", Alimentary Pharmacology and Therapeutics, vol. 43, pp. 197-212. (Year: 2016).*

Kamke et al., "Rumen metagenome and metatranscriptome analyses of low methane yield sheep reveals a Sharpea-enriched microbiome characterised by lactic acid formation and utilisation", Microbiome, vol. 4(56), pp. 1-16. (Year: 2016).*

Anzilotti, Eillie., Fast Company Website, "This New Probiotic Makes Cow Burps Less Damaging To The Climate", https://www.fastcompany.com/40496239/this-new-probiotic-makes-cow-burps-less-damaging-to-the-climate, (accessed Aug. 2022), pp. 1-5. (Year: 2017).*

Cangussu et al., "Characterization of the Catalytic Structure of Plant Phytase, Protein Tyrosine Phosphatase-Like Phytase, and Histidine Acid Phytases and Their Biotechnological Applications", Enzyme Research, vol. 2018, Article 8240698, pp. 1-12. (Year: 2018).*

Naughton et al., "Microbial biosurfactants: current trends and applications in agricultural and biomedical industries", Journal of Applied Microbiology, vol. 126, pp. 12-28. (Year: 2019).*

Peters, Adele., Fast Company Website, "These probiotics for plants help farms suck up extra carbon dioxide", https://www.fastcompany.com/90303108/these-probiotics-for-plants-help-farms-suck-up-extra-carbon-dioxide, (accessed Aug. 2022), pp. 1-5. (Year: 2019).*

Offei et al., "Unique genetic basis of the distinct antibiotic potency of high acetic acid production in the probiotic yeast Saccharomyces cerevisiae var. boulardii", Genome Research, vol. 29(9), pp. 1478-1494. (Year: 2019).*

De Brito, D., Biosurfactants from renewable raw materials, Universidade do Minho Departamento de Engenharia Biologica, Nov. 2013, pp. 1-93.

De Oliveira, M., et al., "Review: Sophorolipids A Promising Biosurfactant and it's Applications." International Journal of Advanced Biotechnology and Research, 2015, 6(2): 161-174.

Domeignoz-Horta, L.A., et al., "Non-denitrifying nitrous oxide-reducing bacteria—An effective N2O sink in soil." Soil Biology & Biochemistry, 2016, 103: 376-379.

Greppi, A., et al., "Phytase-producing capacity of yeasts isolated from traditional African fermented food products and PHYPk gene expression of Pichia kudriavzevii strains." International Journal of Food Microbiology, 2015, 205: 81-89.

Kurtzman, C.P., et al., "Production of sophorolipid biosurfactants by multiple species of the Starmerella (Candida) bombicolayeast clade." FEMS Microbiol Lett, 2010, 311: 140-146.

Meena, K.R., et al., "Lipopeptides as the Antifungal and Antibacterial Agents: Applications in Food Safety and Therapeutics." BioMed Research International, 2015, 2015(Article ID 473050): 1-9.

Mikulsklm D., et al., "Evaluation of phytic acid utilization by S. cerevisiae strains used in fermentation processes and biomass production." Journal of Basic Microbiology, 2017, 57: 87-91.

Morikawa, M., "Beneficial Biofilm Formation by Industrial Bacteria Bacillus subtilis and Related Species." Journal of Bioscience and Bioengineering, 2006, 101(1): 1-8.

Nitschke, M., et al., "Production and properties of a surfactant obtained from Bacillus subtilis grown on cassava wastewater." Bioresource Technology, 2006, 97: 336-341.

Sen, R., "Biosurfactants: Advances in Experimental Medicine and Biology." Landes Bioscience and Springer Science +Business Media, LLC, 2010, 672: 1-331.

Sharma, A. et al., "A study on biosurfactant production in Lactobacillus and Bacillus sp." Int. J. Curr. Microbiol. App. Sci., 2014, 3(11): 723-733.

Sil, J., et al., "Health Care Applications of Different Biosurfactants: Review." International Journal of Science and Research (IJSR), 2015, 6(10): 41-50.

Government of Western Australia, (2018). "Carbon farming: reducing methane emissions from cattle using feed additives." https://www.agric.wa.gov.au/climate change/carbon-farming-reducing-methane-emissions-cattle-using-feed-additives, Webpage. 5 pages.

Gerber, P.J., et al., (2013). Tackling climate change through livestock—A global assessment of emissions and mitigation opportunities. Food and Agriculture Organization of the United Nations, Rome. Viewed Apr. 5, 2019. http://www.fao.org/3/i3437e/i3437e.pdf, pp. 1-116.

Pidwirny, M. (2006). "The Carbon Cycle". Fundamentals of Physical Geography, 2nd Edition. Viewed Oct. 1, 2018. http://www.physicalgeography.net/fundamentals/9r.html, Webpage. 4 pages.

Storm, Ida M.L.D., A.L.F. Hellwing, N.I. Nielsen, and J. Madsen. (2012). "Methods for Measuring and Estimating Methane Emission from Ruminants." Animals (Basel). Jun. 2(2): 160-183. doi: 10.3390/ani2020160.

United States Environmental Protection Agency, (2016). "Climate Change Indicators in the United States." https://www.epa.gov/sites/production/files/2016-08/documents/climate_indicators_2016.pdf, 96 pages.

United States Environmental Protection Agency, (2016). "Overview of Greenhouse Gases." Greenhouse Gas Emissions. https://www.epa.gov/ghgemissions/overview-greenhouse-gases, Webpage. 4 pages.

Patra, A., et al., "Rumen methanogens and mitigation of methane emission by anti-methanogenic compounds and substances." Journal of Animal Science and Biotechnology, 2017, 8(13): 1-18.

* cited by examiner

PASTURE TREATMENTS FOR ENHANCED CARBON SEQUESTRATION AND REDUCTION IN LIVESTOCK-PRODUCED GREENHOUSE GAS EMISSIONS

CROSS-REFERENCE TO RELATED APPLICATIONS

This application claims priority to U.S. Provisional Patent Applications No. 62/833,355, filed Apr. 12, 2019; No. 62/885,876, filed Aug. 13, 2019; and 62/967,907 filed Jan. 30, 2020, each of which is incorporated herein by reference in its entirety.

BACKGROUND OF THE INVENTION

Gases that trap heat in the atmosphere are called "greenhouse gases," or "GHG," and include carbon dioxide, methane, nitrous oxide and fluorinated gases (EPA report 2016 at 6).

Carbon dioxide ($CO_2$) enters the atmosphere through burning fossil fuels (coal, natural gas, and oil), solid waste, trees and wood products, and also as a result of certain chemical reactions, e.g., the manufacture of cement. Carbon dioxide is removed from the atmosphere by, for example, absorption by plants as part of the biological carbon cycle.

Nitrous oxide ($N_2O$) is emitted during industrial activities and during combustion of fossil fuels and solid waste. In agriculture, over-application of nitrogen-containing fertilizers and poor soil management practices can also lead to increased emissions of nitrous oxide and other nitrogen-based gases.

Fluorinated gases including, e.g., hydrofluorocarbons, perfluorocarbons, sulfur hexafluoride, and nitrogen trifluoride are synthetic, powerful greenhouse gases that are emitted from a variety of industrial processes.

Methane (CH4) is emitted during the production and transport of coal, natural gas, and oil. Furthermore, other agricultural practices, and the decay of organic waste in lagoons and municipal solid waste landfills can produce methane emissions. Notably, however, methane emissions also result from production of livestock animals, many of whose digestive systems comprise methanogenic microorganisms (Overview of Greenhouse Gases 2016).

Based on recent measurements from monitoring stations around the world and measurement of older air from air bubbles trapped in layers of ice from Antarctica and Greenland, global atmospheric concentrations of GHGs have risen significantly over the last few hundred years (EPA report 2016 at, e.g., 6, 15).

Especially since the Industrial Revolution began in the 1700s, human activity has contributed to the amount of GHGs in the atmosphere by burning fossil fuels, cutting down forests, and conducting other activities. Many GHGs emitted into the atmosphere remain there for long periods of time ranging from a decade to many millennia. Over time these gases are removed from the atmosphere by chemical reactions or by emissions sinks, such as the oceans and vegetation that absorb GHGs from the atmosphere.

World leaders have attempted to curb the increase of GHG emissions through treaties and other inter-state agreements. One such attempt is through the use of carbon credit systems. A carbon credit is a generic term for a tradable certificate or permit representing the right to emit one ton of carbon dioxide, or an equivalent GHG. In a typical carbon credit system, a governing body sets quotas on the amount of GHG emissions an operator can produce. Exceeding these quotas requires the operator to purchase extra allowances from other operators who have not used all of their carbon credits.

One goal of carbon credit systems is to encourage companies to invest in more green technology, machinery and practices in order to benefit from the trade of these credits. Under the Kyoto Protocol of the United Nations Framework Convention On Climate Change (UNFCCC), a large number of countries have agreed to be bound internationally by policies for GHG reduction, including through trade of emissions credits. While the United States is not bound by the Kyoto Protocol, and while there is no central national emissions trading system in the U.S., some states, such as California and a group of northeastern states, have begun to adopt such trading schemes.

Another attempt to reduce atmospheric GHGs, in particular, methane emissions, has involved the use of feed additives or supplements in livestock production. Ruminant livestock, such as, for example, cattle, sheep, buffalo, goats, deer and camels, are unique because of their four stomach compartments: the reticulum, rumen, omasum and abomasum. The rumen, in particular, is a large, hollow organ where microbial fermentation of ingested substances, such as fibrous plant material, occurs. This organ can hold 40-60 gallons of material, with an estimated microbial concentration of 150 billion microbes per teaspoon of rumen contents.

The rumen functions as a fermentation vessel for certain bacteria that produce gaseous fermentation by-products, as well as protozoa that share a symbiotic relationship with these bacteria to provide hydrogen required for, e.g., reducing carbon dioxide to methane. Thus, the digestive processes occurring within the rumen promote the development of gases, including hydrogen, oxygen, nitrogen, methane and carbon dioxide. Carbon dioxide and methane make up the largest portion of gases produced in the rumen, with carbon dioxide comprising about two to three times the amount of methane.

In addition to gut fermentation, livestock manure can also be a source of GHG emissions. Cattle manure, for example, contains two components that can lead to GHG emissions during storage and processing: organic matter that can be converted into methane emissions, and nitrogen that leads indirectly to nitrous oxide emissions. Methane is released when methanogenic bacteria decompose the organic material in the manure as it is being held in lagoons or holding tanks. Additionally, nitrogen in the form of ammonia ($NH_3$) is released from manure during storage and processing. Ammonia can later be transformed into nitrous oxide. (Gerber et al. 2013).

Currently, approaches for reducing cattle methane emissions include defaunation of the rumen and even vaccination of cattle against methanogens. The downside to these strategies, however, is that they may reduce the number of beneficial rumen microbes, and the methods may be short-lived due to microbial adaptation, as well as cost and inefficiency of application.

Other strategies have involved dietary modification, particularly for cows grazing pasture, in order to manipulate ruminal fermentation by, for example, directly inhibiting methanogens and protozoa, or by redirecting hydrogen ions away from the methanogens to reduce methanogenesis. Such dietary modifications include, for example, the addition of probiotics, acetogens, bacteriocins, ionophores (e.g., monensin and lasalocid), organic acids and/or plant extracts (e.g., tannins and/or seaweed), to feed. (Ishler 2016).

The cattle industry is important for the production of meats and dairy products; however, growing concerns over climate change and a need for reducing GHG emissions calls for improved approaches for producing cattle with reduced GHG emissions.

BRIEF SUMMARY OF THE INVENTION

The subject invention provides compositions and methods for reducing atmospheric greenhouse gas emissions using beneficial microorganisms. More specifically, the subject invention provides multi-purpose compositions that, when applied to a livestock animal's feed and/or to grazing fields and pastures, lead to a reduction in greenhouse gas (GHG) emissions that would have otherwise occurred as a result of livestock production.

In specific embodiments, the subject invention provides a composition for reducing atmospheric GHG emissions and/or emissions of GHG precursors, wherein the composition comprises one or more beneficial microorganisms and/or one or more microbial growth by-products. In preferred embodiments, the beneficial microorganisms are non-pathogenic fungi, yeasts and/or bacteria.

Advantageously, in preferred embodiments, the subject compositions can reduce atmospheric GHG in multiple ways. In one embodiment, the compositions can help reduce deleterious enteric atmospheric gases in the digestive systems of livestock animals by controlling, and/or inhibiting methanogenesis by, methanogenic gut bacteria and/or their protozoal symbionts. Furthermore, the compositions can enhance plant growth when applied to grazing fields and pastures, thereby producing carbon sinks for the sequestration of carbon.

In certain preferred embodiments, the composition comprises one or more bacteria and/or growth by products thereof. The bacteria can be, for example, a *Myxococcus* sp. (e.g., *M. xanthus*), and/or one or more *Bacillus* spp. bacteria. In certain embodiments, the *Bacillus* spp. are *B. amyloliquefaciens, B. subtilis* and/or *B. licheniformis*. Bacteria can be used in spore form, as vegetative cells, and/or as a mixture thereof.

In one embodiment, the composition comprises *B. amyloliquefaciens*. In a preferred embodiment, the strain of *B. amyloliquefaciens* is *B. amyloliquefaciens* NRRL B-67928 ("*B. amy*").

In certain embodiments, the composition comprises one or more fungi and/or one or more growth by-products thereof. The fungi can be, for example, *Pleurotus* spp. fungi, e.g., *P. ostreatus* (oyster mushrooms), *Lentinula* spp. fungi, e.g., *L. edodes* (shiitake mushrooms), and/or *Trichoderma* spp. fungi, e.g., *T. viridae*. The fungi can be in the form of live or inactive cells, mycelia, spores and/or fruiting bodies. The fruiting bodies, if present, can be, for example, chopped and/or blended into granules and/or a powder form.

In one embodiment, the composition comprises one or more yeasts and/or one or more growth by-products thereof. The yeast(s) can be, for example, *Wickerhamomyces anomalus, Saccharomyces* spp. (e.g., *S. cerevisiae* and/or *S. boulardii*), *Starmerella bombicola, Meyerozyma guilliermondii, Pichia occidentalis, Monascus purpureus*, and/or *Acremonium chrysogenum*. The yeast(s) can be in the form of live or inactive cells or spores, as well as in the form of dried and/or dormant cells (e.g., a yeast hydrolysate).

In one exemplary embodiment, the composition comprises *B. amy*. In one exemplary embodiment, the composition comprises *B. amy* and *P. ostreatus*. In one exemplary embodiment, the composition comprises *B. amy* and *S. boulardii*.

In one exemplary embodiment, the composition comprises *P. ostreatus*. In one exemplary embodiment, the composition comprises *S. boulardii*. In one exemplary embodiment, the composition comprises *P. ostreatus* and *S. boulardii*.

In one exemplary embodiment, the composition comprises *B. amy, P. ostreatus*, and *S. boulardii*.

In one exemplary embodiment, the composition comprises *L. edodes* and *W. anomalus*.

In certain embodiments, the composition comprises a germination enhancer for enhancing germination of spore-form microorganisms used in the composition. In specific embodiments, the germination enhancers are amino acids, such as, for example, L-alanine and/or L-leucine. In one embodiment, the germination enhancer is manganese.

In one embodiment, the composition comprises one or more fatty acids. In certain preferred embodiments, the fatty acid is a saturated long-chain fatty acid, having a carbon backbone of 14-20 carbons, such as, for example, myristic acid, palmitic acid and/or stearic acid. In some embodiments, a combination of two or more saturated long-chain fatty acids is included in the composition. In some embodiments, a saturated long-chain fatty acid can inhibit methanogenesis and/or increase cell membrane permeability of methanogens in the rumen.

In one embodiment, the composition comprises a microbial growth by-product. The microbial growth by-product can be produced by the microorganisms of the composition, and/or they can be produced separately and added to the composition.

In one embodiment, the growth by-product has been purified from the fermentation medium in which it was produced. Alternatively, in one embodiment, the growth by-product is utilized in crude form. The crude form can comprise, for example, a liquid supernatant resulting from cultivation of a microbe that produces the growth by-product of interest, including residual cells and/or nutrients.

The growth by-products can include metabolites or other biochemicals produced as a result of cell growth, including, for example, amino acids, peptides, proteins, enzymes, biosurfactants, solvents and/or other metabolites.

In one embodiment, the composition comprises lovastatin. Lovastatin is a growth by-product of *Pleurotus* ostreatus, and inhibits methanogenic archaea via inhibition of the enzyme involved in formation of the isoprenoid building blocks that are essential for methanogen cell membrane synthesis, HMG-CoA reductase. In one embodiment, the composition comprises lovastatin in purified form, either with or without the *Pleurotus* fungus.

In one embodiment, the composition comprises live *Lentinula edodes*, which can inhibit HMG-CoA reductase activity without production of lovastatin.

In one embodiment, the composition comprises red yeast rice, or koji, the fermented rice product of *Monascus purpureus*. Red yeast rice comprises the growth by-product monacolin K, which has a similar structure to lovastatin and has similar ability to inhibit HMG-CoA reductase activity.

In one embodiment, the composition comprises valine. Valine is an amino acid produced by *Wickerhamomyces anomalus* and *Saccharomyces* spp., which helps support the growth and health of livestock animals, as well as reduces the amount of nitrogen (e.g., ammonium) excretion by the animals' digestive processes. In one embodiment, the composition comprises valine in purified form, either with or without a microorganism that produced it.

In some embodiments, the composition can comprise additional components known to reduce methanogenesis by methanogens, such as, for example, seaweed (e.g., *Asparagopsis taxiformis*), kelp, 3-nitrooxypropanol, anthraquinones, ionophores (e.g., monensin and/or lasalocid), polyphenols (e.g., saponins, tannins), organosulfurs (e.g., garlic extract), flavonoids (e.g., quercetin, rutin, kaempferol, naringin, and anthocyanidins; bioflavonoids from green citrus fruits, rose hips and black currants), carboxylic acid, and/or terpenes (e.g., d-limonene, pinene and citrus extracts).

In one embodiment, the subject composition can comprise one or more additional substances and/or nutrients to supplement livestock animals' and/or plants' nutritional needs and promote health and/or well-being in the livestock animal and/or plant, such as, for example, prebiotics and/or sources of amino acids (including essential amino acids), peptides, proteins, vitamins, microelements, fats, fatty acids, lipids, carbohydrates, sterols, enzymes, and minerals such as calcium, magnesium, phosphorus, potassium, sodium, chlorine, sulfur, chromium, cobalt, copper, iodine, iron, manganese, molybdenum, nickel, selenium, and zinc. In some embodiments, the microorganisms of the composition produce and/or provide these substances.

In preferred embodiments, the subject invention provides a method for reducing emissions of methane, carbon dioxide, and/or other deleterious atmospheric gases, and/or precursors thereof (e.g., nitrogen and ammonia, which are precursors of nitrous oxide), wherein a composition comprising one or more beneficial microorganisms and/or one or more microbial growth by-products is applied to a field or pasture. Preferably, the composition is a multi-purpose composition according to embodiments of the subject invention. In certain specific embodiments, the livestock animals are ruminants.

In a specific embodiment, the field or pasture is a food source for the livestock animals, comprising grasses and/or other plants upon which the livestock animals graze. The livestock animals are placed in the field or pasture to graze, thereby ingesting the composition in addition to ingesting the grasses and/or other plants in the pasture.

Advantageously, in preferred embodiments, the methods result in a reduction of methanogenic bacteria and/or protozoa present in the livestock animal's digestive system, particularly, the rumen. In certain embodiments, the methods result in a decrease in the amount of nitrous oxide precursor compounds produced (e.g., nitrogen and/or ammonia), and/or a decrease in the amount of carbon dioxide produced by the animal's digestive and metabolic processes. In certain embodiments, the methods can also result in a reduction of GHG emissions from the livestock animal's waste (e.g., manure).

In certain embodiments, the methods can also be used for enhancing soil carbon sequestration, wherein the soil of a field or pasture is inoculated with one or more beneficial microorganisms that enhance the amount of plant and microbial biomass in the pasture or field, thereby transforming the field or pasture into a carbon sink.

In one embodiment, the composition is applied either as a liquid or a dried product. In one embodiment the composition is broadcast, either in the liquid or dried form, over the field or pasture using, for example, an irrigation system. Additionally, the composition can be applied using a manual spreader, such as a broadcast spreader, a drop spreader, a handheld spreader, or a handheld sprayer.

In certain embodiments, the methods further comprise adding the composition to drinking water and/or supplemental feed that is provided to the grazing livestock animals.

In one embodiment, the composition is formulated into the supplemental feed, wherein the composition is added to standard raw food ingredients utilized in producing processed wet and/or dry animal feed.

In some embodiments, the methods of the subject invention can be utilized by a livestock producer for reducing carbon credit usage. Thus, in certain embodiments, the subject methods can further comprise conducting measurements to assess the effect of the method on reducing the generation of methane, carbon dioxide and/or other deleterious atmospheric gases, and/or precursors thereof (e.g., nitrogen and/or ammonia); to assess the effect of the method on the control of methanogens and/or protozoa in the livestock animal's digestive system and/or waste; and/or to assess the effect of the method on the sequestration of carbon in the soil of the field or pasture, using standard techniques in the art.

DETAILED DESCRIPTION OF THE INVENTION

Figure 1:
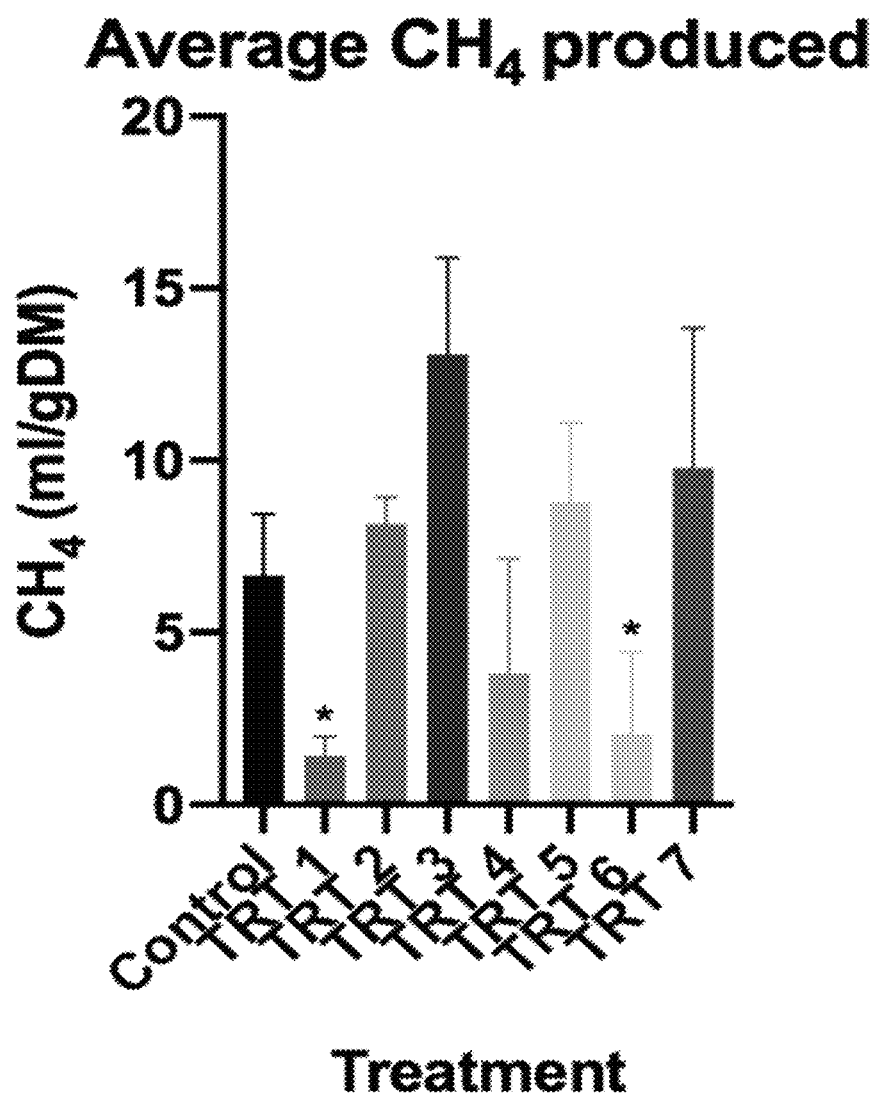
FIG. 1 shows the results of in-vitro studies of compositions according to embodiments of the subject invention to determine their ability to reduce enteric methane emissions from cattle rumen. The abbreviation "TRT" is used to refer to "Treatment."

The subject invention provides compositions and methods for reducing atmospheric greenhouse gas emissions using beneficial microorganisms. More specifically, the subject invention provides multi-purpose compositions for feeding domesticated animals that, for example, when applied to the animals' feed and/or to grazing fields and pastures, lead to a reduction in greenhouse gas emissions that would have otherwise occurred as a result of livestock production.

Selected Definitions

As used herein, a "biofilm" is a complex aggregate of microorganisms, such as bacteria, wherein the cells adhere to each other and/or to a surface. The cells in biofilms are physiologically distinct from planktonic cells of the same organism, which are single cells that can float or swim in liquid medium.

As used herein, the term "control" used in reference to an undesirable microorganism (e.g., a methanogen) extends to the act of killing, disabling, immobilizing and/or reducing the population numbers of the microorganism, and/or otherwise rendering the microorganism incapable of carrying out the processes that are undesirable (e.g., methane production).

As used herein, a "domesticated" animal is an animal of a species that has been influenced, bred, tamed, and/or controlled over a sustained number of generations by humans, such that a mutualistic relationship exists between the animal and the human. In preferred embodiments, domesticated animals are "livestock," which include animals raised in an agricultural or industrial setting to produce commodities such as food, fiber and labor. Types of animals included in the term livestock can include, but are not limited to, alpacas, llamas, beef and dairy cattle, bison, pigs, sheep, goats, horses, digs, mules, asses, camels, chickens, turkeys, ducks, geese, guinea fowl, and squabs.

In certain preferred embodiments, the livestock are "ruminants," or mammals that utilize a compartmentalized stomach suited for fermenting plant-based foods prior to digestion with the help of a specialized gut microbiome. Ruminants include, for example, bovines (e.g., bison, bongo, buffalo, cow, bull, ox, kudu, imbabala, water buffalo, yak, and zebu), sheep, goats, ibex, giraffes, deer, elk, moose, camels, caribou, reindeer, antelope, gazelle, impala, wildebeest, and some kangaroos.

As used herein, an "isolated" or "purified" molecule or other compound is substantially free of other compounds, such as cellular material, with which it is associated in nature. For example, a purified or isolated polynucleotide (ribonucleic acid (RNA) or deoxyribonucleic acid (DNA)) is free of genes or sequences that flank it in its naturally-occurring state. A purified or isolated polypeptide is free of the amino acids or sequences that flank it in its naturally-occurring state. A purified or isolated microbial strain is removed from the environment in which it exists in nature, or in which it was produced. Thus, the isolated strain may exist as, for example, a biologically pure culture, or as spores (or other forms of the strain) in association with a carrier.

In certain embodiments, purified compounds are at least 60% by weight the compound of interest. Preferably, the preparation is at least 75%, more preferably at least 90%, and most preferably at least 99%, by weight the compound of interest. For example, a purified compound is one that, preferably, is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

As used herein, "ionophores" are carboxylic polyether non-therapeutic antibiotics that disrupt the ion concentration gradient ($Ca^{2+}$, $K^+$, $H^+$, $Na^+$) across microorganisms, which causes them to enter a futile ion cycle. The disruption of the ion concentration prevents the microorganism from maintaining normal metabolism and causes the microorganism to expend extra energy. Ionophores function by selecting against or negatively affecting the metabolism of gram-positive bacteria, such as methanogens, and protozoa in the rumen.

A "metabolite" refers to any substance produced by metabolism (e.g., a growth by-product) or a substance necessary for taking part in a particular metabolic process. A metabolite can be an organic compound that is a starting material, an intermediate in, or an end product of metabolism. Examples of metabolites can include, but are not limited to, enzymes, toxins, acids, solvents, alcohols, proteins, carbohydrates, vitamins, minerals, microelements, amino acids, polymers, and surfactants.

As used herein, a "methanogen" is a microorganism that produces methane gas as a by-product of metabolism. Methanogens are archaea that can be found in the digestive systems and metabolic waste of ruminant animals and non-ruminant animals (e.g., pigs, poultry and horses). Examples of methanogens include, but are not limited to, *Methanobacterium* spp. (e.g., *M. formicicum*), *Methanobrevibacter* spp. (e.g., *M. ruminantium*), *Methanococcus* spp. (e.g., *M. paripaludis*), *Methanoculleus* spp. (e.g., *M. bourgensis*), *Methanoforens* spp. (e.g., *M. siordalenmirensis*), *Methanofollis liminatans*, *Methanogenium wolfei*, *Methanomicrobium* spp. (e.g., *M. mobile*), *Methanopyrus kandleri*, *Methanoregula boonei*, *Methanosaeta* spp. (e.g., *M. concilii*, *M. thermophile*), *Methanosarcina* spp. (e.g., *M. barkeri*, *M. mazeii*), *Methanosphaera stadtmanae*, *Methanospirillium hungatei*, *Methanothermobacter* spp., and/or *Methanothrix sochngenii*.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

As used herein, "reduction" means a negative alteration and "increase" means a positive alteration, wherein the positive or negative alteration is at least 0.25%, 0.5%, 1%, 5%, 10%, 15%, 20%, 25%, 30%, 35%, 40%, 45%, 50%, 55%, 60%, 65%, 70%, 75%, 80%, 85%, 90%, 95% or 100%.

The transitional term "comprising," which is synonymous with "including," or "containing," is inclusive or open-ended and does not exclude additional, un-recited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention. Use of the term "comprising" contemplates other embodiments that "consist" or "consist essentially of" the recited component(s).

Unless specifically stated or obvious from context, as used herein, the term "or" is understood to be inclusive. Unless specifically stated or obvious from context, as used herein, the terms "a," "and" and "the" are understood to be singular or plural.

Unless specifically stated or obvious from context, as used herein, the term "about" is understood as within a range of normal tolerance in the art, for example within 2 standard deviations of the mean. About can be understood to be within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

All references cited herein are hereby incorporated by reference in their entirety.

Multi-Purpose Compositions

In certain embodiments, the subject invention provides a multi-purpose composition for reducing atmospheric GHG emissions and/or emissions of GHG precursors, wherein the composition comprises one or more beneficial microorganisms and/or one or more microbial growth by-products.

In certain embodiments, the composition is a "microbe-based composition," meaning a composition that comprises components that were produced as the result of the growth of microorganisms or other cell cultures. Thus, the microbe-based composition may comprise the microbes themselves and/or by-products of microbial growth. The microbes may be in a vegetative state, in spore form, in mycelial form, in any other form of microbial propagule, or a mixture of these. The microbes may be planktonic or in a biofilm form, or a mixture of both. The by-products of growth may be, for example, metabolites, cell membrane components, expressed proteins, and/or other cellular components. The microbes may be intact or lysed. The cells may be totally absent, or present at, for example, a concentration of $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$ or more CFU per milliliter of the composition.

Advantageously, in preferred embodiments, the subject multi-purpose compositions can alter the digestive processes of ruminant animals, resulting in decreased enteric atmospheric gas production. For example, the compositions can control, and/or inhibit methanogenesis by, methanogenic bacteria in the rumen and/or their protozoal symbionts. In some embodiments, the subject compositions can also help reduce enteric carbon dioxide production. In some embodiments, the composition can also enhance the growth and health of livestock, while enabling more complete transformation of protein sources in feed to reduce nitrogen release in the animals' waste in the form of, e.g., ammonia. Furthermore, the compositions can enhance plant growth when applied to grazing fields and pastures, thereby producing carbon sinks for the sequestration of carbon.

In preferred embodiments, the beneficial microorganisms of the subject compositions are non-pathogenic fungi, yeasts and/or bacteria. The beneficial microorganisms may be in an active, inactive and/or dormant.

The microorganisms and/or microbial growth by-products of the subject compositions can be obtained through cultivation processes ranging from small to large scale. These cultivation processes include, but are not limited to, submerged cultivation/fermentation, solid state fermentation (SSF), and modifications, hybrids and/or combinations thereof.

In certain embodiments, the compositions of the subject invention can comprise the fermentation medium in which the beneficial microorganism and/or the growth by-product was produced.

The microorganisms of the subject invention may be natural, or genetically modified microorganisms. For example, the microorganisms may be transformed with specific genes to exhibit specific characteristics. The microorganisms may also be mutants of a desired strain. As used herein, "mutant" means a strain, genetic variant or subtype of a reference microorganism, wherein the mutant has one or more genetic variations (e.g., a point mutation, missense mutation, nonsense mutation, deletion, duplication, frameshift mutation or repeat expansion) as compared to the reference microorganism. Procedures for making mutants are well known in the microbiological art. For example, UV mutagenesis and nitrosoguanidine are used extensively toward this end.

In one specific embodiment, the composition comprises about $1\times10^6$ to about $1\times10^{13}$, about $1\times10^7$ to about $1\times10^{12}$, about $1\times10^8$ to about $1\times10^{11}$, or about $1\times10^9$ to about $1\times10^{10}$ CFU/ml of each species of microorganism present in the composition.

In certain embodiments, the amount of microorganisms in one application of the composition totals about 40 to 70 grams per head (individual animals in a cattle herd), or about 45 to about 65 grams per head, or about 50 to about 60 grams per head.

In one embodiment, the composition comprises about 1 to 100% microorganisms total by volume, about 10 to 90%, or about 20 to 75%.

In certain preferred embodiments, the composition comprises one or more bacteria and/or growth by products thereof. The bacteria can be, for example, a *Myxococcus* sp. (e.g., *M. xanthus*), and/or one or more *Bacillus* spp. bacteria. In certain embodiments, the *Bacillus* spp. are *B. amyloliquefaciens*, *B. subtilis* and/or *B. licheniformis*. Bacteria can be used in spore form, as vegetative cells, and/or as a mixture thereof.

In one embodiment, the composition comprises *B. amyloliquefaciens*. In some embodiments, *B. amyloliquefaciens* can serve as a probiotic in cattle, to increase body weight gain, increase feed intake and conversion, and increase growth hormone (e.g., GH/IGH-1) levels. Additionally, *B. amyloliquefaciens* can promote the growth of other beneficial microbes (e.g., producers of fatty acids) while decreasing the amount of potential pathogenic microbes in an animal's gut, e.g., by producing anti-microbial lipopeptide biosurfactants. In some embodiments, a dosage of $4\times10^{10}$ CFU/day of *B. amyloliquefaciens* is administered to an animal as part of a composition of the subject invention.

In a preferred embodiment, the strain of *B. amyloliquefaciens* is *B. amyloliquefaciens* NRRL B-67928 ("*B. amy*").

A culture of the *B. amyloliquefaciens* "*B. amy*" microbe has been deposited with the Agricultural Research Service Northern Regional Research Laboratory (NRRL) Culture Collection, 1815 N. University St., Peoria, Ill., USA. The deposit has been assigned accession number NRRL B-67928 by the depository and was deposited on Feb. 26, 2020.

The subject culture has been deposited under conditions that assure that access to the culture will be available during the pendency of this patent application to one determined by the Commissioner of Patents and Trademarks to be entitled thereto under 37 CFR 1.14 and 35 U.S.C 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

In some embodiments, *B. lichenformis* can reduce methane production by methanogens, and inhibit the methanogenic bacteria themselves through production of propionic acid and other metabolites, such as lipopeptide biosurfactants. Additionally, *B. licheniformis* can help decrease the concentration of ammonia in cattle ruminal fluids while helping increase milk protein production. In pigs, *B. lichenformis* and *B. subtilis* can help increase fecal *Lactobacillus* counts increase the digestibility of nitrogen, and a decrease the emission of ammonia and mercaptans. In some embodiments, a dosage of 2×10$^{10}$ CFU/day of *B. lichenformis* is administered to an animal as part of a composition of the subject invention.

In one embodiment, the beneficial microorganisms are yeasts and/or fungi. Yeast and fungus species suitable for use according to the current invention, include *Acaulospora, Acremonium chrysogenum, Aspergillus, Aureobasidium* (e.g., *A. pullulans*), *Blakeslea, Candida* (e.g., *C. albicans, C. apicola, C. batistae, C. bombicola, C. floricola, C. kuoi, C. riodocensis, C. nodaensis, C. stellate*), *Cryptococcus, Debaryomyces* (e.g., *D. hansenii*), *Entomophthora, Hanseniaspora* (e.g., *H. uvarum*), *Hansenula, Issatchenkia, Kluyveromyces* (e.g., *K. phaffii*), *Lentinula* spp. (e.g., *L. edodes*), *Meyerozyma* (e.g., *M. guilliermondii*), *mycorrhiza* (e.g., *Leccinum* spp., *Suillus* spp., *Monascus purpureus, Mortierella, Mucor* (e.g., *M. piriformis*), *Penicillium, Phythium, Phycomyces, Pichia* (e.g., *P. anomala, P. guilliermondii, P. occidentalis, P. kudriavzevii*), *Pleurotus* (e.g., *P. ostreatus P. ostreatus, P. sajorcaju, P. cystidiosus, P. cornucopiae, P. pulmonarius, P. tuberregium, P. citrinopileatus* and *P. flabellatus*), *Pseudozyma* (e.g., *P. aphidis*), *Rhizopus, Rhodotorula* (e.g., *R. bogoriensis*); *Saccharomyces* (e.g., *S. cerevisiae, S. boulardii, S. torula*), *Starmerella* (e.g., *S. bombicola*), *Torulopsis, Thraustochytrium, Trichoderma* (e.g., *T. reesei, T. harzianum, T. viridae*), *Ustilago* (e.g., *U. maydis*), *Wickerhamiella* (e.g., *W. domericqiae*), *Wickerhamomyces* (e.g., *W. anomalus*), *Williopsis* (e.g., *W. mrakii*), *Zygosaccharomyces* (e.g., *Z. bailii*), and others.

In certain specific embodiments, the composition comprises one or more fungi and/or one or more growth by-products thereof. The fungi can be, for example, *Pleurotus* spp. fungi, e.g., *P. ostreatus* (oyster mushrooms), *Lentinula* spp. fungi, e.g., *L. edodes* (shiitake mushrooms), and/or *Trichoderma* spp. fungi, e.g., *T. viridae* or *T. harzianum*. The fungi can be in the form of live or inactive cells, mycelia, spores and/or fruiting bodies. The fruiting bodies, if present, can be, for example, chopped and/or blended into granules and/or a powder form.

In certain specific embodiments, the composition comprises one or more yeasts and/or one or more growth by-products thereof. The yeast(s) can be, for example, *Wickerhamomyces anomalus, Saccharomyces* spp. (e.g., *S. cerevisiae* and/or *S. boulardii*), *Starmerella bombicola, Meyerozyma guilliermondii, Pichia occidentalis, Monascus purpureus*, and/or *Acremonium chrysogenum*. The yeast(s) can be in the form of live or inactive cells or spores, as well as in the form of dried and/or dormant cells (e.g., a yeast hydrolysate).

In one exemplary embodiment, the comprises *B. amy.* In one exemplary embodiment, the composition comprises *S. boulardii* and *P. ostreatus*. In one exemplary embodiment, the composition comprises *B. amy* and one or both of *S. boulardii* and *P. ostreatus*.

In certain embodiments, the composition comprises a germination enhancer for enhancing germination of spore-form microorganisms used in the composition. In specific embodiments, the germination enhancers are amino acids, such as, for example, L-alanine and/or L-leucine. In one embodiment, the germination enhancer is manganese.

In one embodiment, the composition comprises one or more fatty acids. In certain preferred embodiments, the fatty acid is a saturated long-chain fatty acid, having a carbon backbone of 14-20 carbons, such as, for example, myristic acid, palmitic acid or stearic acid. In some embodiments, a combination of two or more saturated long-chain fatty acids is included in the composition. In some embodiments, a saturated long-chain fatty acid can inhibit methanogenisis and/or increase cell membrane permeability of methanogens in the rumen.

In one embodiment, the composition comprises a microbial growth by-product. The microbial growth by-product can be produced by the microorganisms of the composition, and/or they can be produced separately and added to the composition.

In one embodiment, the growth by-product has been purified from the fermentation medium in which it was produced. Alternatively, in one embodiment, the growth by-product is utilized in crude form. The crude form can comprise, for example, a liquid supernatant resulting from cultivation of a microbe that produces the growth by-product of interest, including residual cells and/or nutrients.

The growth by-products can include metabolites or other biochemicals produced as a result of cell growth, including, for example, amino acids, peptides, proteins, enzymes, biosurfactants, solvents and/or other metabolites.

In one embodiment, the composition comprises *Pleurotus ostreatus*, a culture of which can contain concentrations of about 2.5% to 3.0%, or 2.8% lovastatin (dry weight).

Lovastatin is a polyketide growth by-product of *Pleurotus*, and inhibits methanogenic archaea via inhibition of the enzyme involved in formation of the isoprenoid building blocks that are essential for their cell membrane synthesis, HMG-CoA reductase. Advantageously, lovastatin can inhibit the growth of methanogens without adverse effects on other cellulolytic bacteria in the rumen. In one embodiment, the composition comprises lovastatin in purified form, either with or without the *Pleurotus* fungus.

In one embodiment, the composition comprises live *Lentinula edodes*, which can inhibit HMG-CoA reductase activity without production of lovastatin.

In one embodiment, the composition comprises *Trichoderma viridae* and/or *Acremonium chrysogenum*, which also produce statins similar to lovastatin.

In one embodiment, the composition comprises red yeast rice, or koji, the fermented rice product of *Monascus purpureus*. Red yeast rice comprises monacolin K, which has a similar structure to lovastatin and has the ability to inhibit HMG-CoA reductase activity.

In certain embodiments, the composition comprises a culture of *Wickerhamomyces anomalus* and/or *Saccharomyces* spp. yeasts. These yeasts boost acetogenesis and hydrogen utilization by acetogenic bacteria within a ruminant digestive system. Advantageously, this results in less hydrogen availability for methanogenic microorganism to carry out processes in which methane is produced, without negatively affecting the digestive health of the animal. Thus, in one embodiment, the presence of *Wickerhamomyces anomalus* and/or *Saccharomyces* spp. yeast (e.g., *S. cerevisiae* and/or *S. boulardii*), and/or growth by-products thereof, in the composition boosts the amount of acetogenic bacteria in a ruminant animal's gut microbiome, and/or decreases the amount of methanogenic bacteria therein.

Additionally, *Wickerhamomyces anomalus* produces phytase, an enzyme useful for improved digestion and bioavailability of phosphorus from feed, as well as killer toxins (e.g., exo-β-1,3-glucanase) useful for controlling pathogenic microorganisms.

In one embodiment, the composition comprises synthetic or biologically produced amino acids. In a specific embodiment, the amino acid is valine. Valine is an amino acid produced by *Wickerhamomyces anomalus* and *Saccharomyces* spp., which helps support the growth and health of livestock animals, and enables more complete transformation of protein sources in feed to reduce the amount of nitrogen excreted in their waste, in the form of, for example, ammonia. In one embodiment, the composition comprises valine in purified form, either with or without a yeast that produces it.

In some embodiments, the composition can comprise additional components known to reduce methane in the rumen, such as, for example, seaweed (e.g., *Asparagopsis taxiformis*), kelp, 3-nitrooxypropanol, anthraquinones, ionophores (e.g., monensin and/or lasalocid), polyphenols (e.g., saponins, tannins), organosulfurs (e.g., garlic extract), flavonoids (e.g., quercetin, rutin, kaempferol, naringin, and anthocyanidins; bioflavonoids from green citrus fruits, rose hips and black currants), carboxylic acid, and/or terpenes (e.g., d-limonene, pinene and citrus extracts).

In one embodiment, the subject composition can comprise one or more additional substances and/or nutrients to supplement the nutritional needs of the livestock animal and/or of the plants in the field or pasture, such as, for example, sources of amino acids (including essential amino acids), peptides, proteins, vitamins, microelements, fats, fatty acids, lipids, carbohydrates, sterols, enzymes, and minerals such as calcium, magnesium, phosphorus, potassium, sodium, chlorine, sulfur, chromium, cobalt, copper, iodine, iron, manganese, molybdenum, nickel, selenium, and zinc. In some embodiments, the microorganisms of the composition produce and/or provide these substances.

In one embodiment, the composition can further comprise one or more biosurfactants. Biosurfactants are a structurally diverse group of surface-active substances produced by microorganisms, which are biodegradable and can be efficiently produced using selected organisms on renewable substrates. All biosurfactants are amphiphiles. They consist of two parts: a polar (hydrophilic) moiety and non-polar (hydrophobic) group. The common lipophilic moiety of a biosurfactant molecule is the hydrocarbon chain of a fatty acid, whereas the hydrophilic part is formed by ester or alcohol groups of neutral lipids, by a carboxylate group of fatty acids or amino acids (or peptides), an organic acid in the case of flavolipids, or, in the case of glycolipids, by a carbohydrate.

Due to their amphiphilic structure, biosurfactants increase the surface area of hydrophobic water-insoluble substances, increase the water bioavailability of such substances, and change the properties of bacterial cell surfaces. Biosurfactants accumulate at interfaces, thus reducing interfacial tension and leading to the formation of aggregated micellar structures in solution. Safe, effective microbial biosurfactants reduce the surface and interfacial tensions between the molecules of liquids, solids, and gases. The ability of biosurfactants to form pores and destabilize biological membranes permits their use as antibacterial, antifungal, and hemolytic agents.

Biosurfactants according to the subject invention can include, for example, low molecular weight glycolipids, lipopeptides, flavolipids, phospholipids, and high molecular weight polymers such as lipoproteins, lipopolysaccharide-protein complexes, and polysaccharide-protein-fatty acid complexes.

In one embodiment, the biosurfactant is a glycolipid. Glycolipids can include, for example, sophorolipids, rhamnolipids, cellobiose lipids, mannosylerythritol lipids and trehalose lipids. In one embodiment, the biosurfactant is a lipopeptide. Lipopeptides can include, for example, surfactin, iturin, arthrofactin, viscosin, fengycin, and lichenysin. In certain embodiments, a mixture of biosurfactants is used.

In one embodiment, the biosurfactant has been purified from the fermentation medium in which it was produced. Alternatively, in one embodiment, the biosurfactant is utilized in crude form comprising fermentation broth resulting from cultivation of a biosurfactant-producing microbe. This crude form biosurfactant solution can comprise from about 0.001% to 99%, from about 25% to about 75%, from about 30% to about 70%, from about 35% to about 65%, from about 40% to about 60%, from about 45% to about 55%, or about 50% pure biosurfactant, along with residual cells and/or nutrients.

In one embodiment, the composition can further comprise water. For example, the microorganism and/or growth by-products can be mixed with water and administered to the bovine animal. In another embodiment, the composition can be mixed with a bovine animal's drinking water as, for example, a feed additive and/or supplement. The drinking water composition can comprise, for example, 1 g/L to about 50 g/L of the composition, about 2 g/L to about 20 g/L, or about 5 g/L to about 10 g/L.

In certain embodiments, the composition comprises a carrier that is suitable for oral delivery of the composition to the gastrointestinal tract of a livestock animal. Carriers can be comprised of solid-based, dry materials for formulation into tablet, capsule or powdered form; or the carrier can be comprised of liquid or gel-based materials for formulations into liquid or gel forms.

In one embodiment, the composition can further comprise pre-made wet or dry animal feed, wherein the pre-made food has been cooked and/or processed to be ready for animal consumption. For example, the microorganism and/or growth by-products can be poured onto and/or mixed with the pre-made food, or the microorganism and/or growth by-products can serve as a coating on the outside of dry animal food pieces, e.g., morsels, kibbles or pellets.

In one embodiment, the composition can further comprise raw ingredients for making animal feed, wherein the raw ingredients, together with the microorganism and/or growth by-products, are then cooked and/or processed to make an enhanced dry or wet feed product.

The composition can be added to the wet or day feed and/or raw feed ingredients at a concentration of, for example, about 0.1% to 99%, about 1% to about 75%, or about 5% to about 50% by weight.

As used herein, "dry food" refers to food that contains a limited moisture content, typically in the range of about 5% to about 15% or 20% w/v. Typically, dry processed food comes in the form of small to medium sized individual pieces, e.g., morsels, kibbles, treats, biscuits, nuts, cakes or pellets.

In one embodiment, the composition can further comprise raw ingredients for making animal feed, wherein the raw ingredients, together with the microorganism and/or growth by-products, are then cooked and/or processed to make an enhanced dry or wet feed product. Raw ingredients can include, for example, grains, grasses, roughage, forage, hay, straw, seeds, nuts, crop residue, vegetables, fruits, dried plant matter, and other flavorings, additives and/or sources of nutrients. In one embodiment, the composition is added to the raw food ingredients at a concentration of about 0.1% to about 50%, about 1% to about 25%, or about 5% to about 15% by weight.

The supplemented dry food pieces can comprise consistent concentrations of the composition per piece. In another embodiment, the composition can be utilized as a surface coating on the dry food pieces. Methods known in the art for producing dry processed foods can be used, including pressurized milling, extrusion, and/or pelleting.

In an exemplary embodiment, dry food may be prepared by, e.g., screw extrusion, which includes cooking, shaping and cutting raw ingredients into a specific shape and size in a very short period of time. The ingredients may be mixed into homogenous expandable dough and cooked in an extruder, and forced through a die under pressure and high heat. After cooking, the pellets are then allowed to cool, before optionally being sprayed with a coating. This coating may comprise, for example, liquid fat or digest, including liquid or powdered hydrolyzed forms of an animal tissue such as liver or intestine from, e.g., chicken or rabbit, and/or a nutritional oil. In other embodiments, the pellet is coated using a vacuum enrobing technique, wherein the pellet is subjected to vacuum and then exposed to coating materials after which the release of the vacuum drives the coating materials inside the pellet. Hot air drying can then be employed to reduce the total moisture content to 10% or less.

In one embodiment, the dry food is produced using a "cold" pelleting process, or a process that does not use high heat or steam. The process can use, for example, liquid binders with viscous and cohesive properties to hold the ingredients together without risk of denaturing or degrading important components and/or nutrients in the compositions of the subject invention.

In one embodiment, the composition can be applied to animal fodder, or cut and dried plant matter, such as hay, straw, silage, sprouted grains, legumes and/or grains.

In one embodiment, the composition may be prepared as a spray-dried biomass product. The biomass may be separated by known methods, such as centrifugation, filtration, separation, decanting, a combination of separation and decanting, ultrafiltration or microfiltration.

In one embodiment, the composition has a high nutritional content, for example, comprising up to 50% protein, as well as polysaccharides, vitamins, and minerals. As a result, the composition may be used as part of all of a complete animal feed composition. In one embodiment, the feed composition comprises the subject composition ranging from 15% of the feed to 99% of the feed.

In one embodiment, the subject composition can comprise additional nutrients to supplement an animal's diet and/or promote health and/or well-being in the animal, such as, for example, sources of amino acids (including essential amino acids), peptides, proteins, vitamins, microelements, fats, fatty acids, lipids, carbohydrates, sterols, enzymes, prebiotics, and trace minerals such as, iron, copper, zinc, manganese, cobalt, iodine, selenium, molybdenum, nickel, fluorine, vanadium, tin and silicon.

In some embodiments, the additional nutrients can also promote plant health and growth for the plants in the field or pasture.

Preferred compositions comprise vitamins and/or minerals in any combination. Vitamins for use in a composition of this invention can include for example, vitamins A, E, K3, D3, B1, B3, B6, B12, C, biotin, folic acid, panthothenic acid, nicotinic acid, choline chloride, inositol and para-aminobenzoic acid. Minerals can include, for example, such as calcium, magnesium, phosphorus, potassium, sodium, chlorine, sulfur, chromium, cobalt, copper, iodine, iron, manganese, molybdenum, nickel, selenium, and zinc. Other components may include, but are not limited to, antioxidants, beta-glucans, bile salt, cholesterol, enzymes, carotenoids, and many others. Typical vitamins and minerals are those, for example, recommended for daily consumption and in the recommended daily amount (RDA), although precise amounts can vary. The composition would preferably include a complex of the RDA vitamins, minerals and trace minerals as well as those nutrients that have no established RDA, but have a beneficial role in healthy mammal physiology.

Production of Microorganisms and/or Microbial Growth by-Products

The subject invention utilizes methods for cultivation of microorganisms and production of microbial metabolites and/or other by-products of microbial growth. The subject invention further utilizes cultivation processes that are suitable for cultivation of microorganisms and production of microbial metabolites on a desired scale. These cultivation processes include, but are not limited to, submerged cultivation/fermentation, solid state fermentation (SSF), and modifications, hybrids and/or combinations thereof.

As used herein "fermentation" refers to cultivation or growth of cells under controlled conditions. The growth could be aerobic or anaerobic. In preferred embodiments, the microorganisms are grown using SSF and/or modified versions thereof.

In one embodiment, the subject invention provides materials and methods for the production of biomass (e.g., viable cellular material), extracellular metabolites, residual nutrients and/or intracellular components.

The microbe growth vessel used according to the subject invention can be any fermenter or cultivation reactor for industrial use. In one embodiment, the vessel may have functional controls/sensors or may be connected to functional controls/sensors to measure important factors in the cultivation process, such as pH, oxygen, pressure, temperature, humidity, microbial density and/or metabolite concentration.

In a further embodiment, the vessel may also be able to monitor the growth of microorganisms inside the vessel (e.g., measurement of cell number and growth phases).

Alternatively, a daily sample may be taken from the vessel and subjected to enumeration by techniques known in the art, such as dilution plating technique. Dilution plating is a simple technique used to estimate the number of organisms in a sample. The technique can also provide an index by which different environments or treatments can be compared.

In one embodiment, the method includes supplementing the cultivation with a nitrogen source. The nitrogen source can be, for example, potassium nitrate, ammonium nitrate ammonium sulfate, ammonium phosphate, ammonia, urea, and/or ammonium chloride. These nitrogen sources may be used independently or in a combination of two or more.

The method can provide oxygenation to the growing culture. One embodiment utilizes slow motion of air to remove low-oxygen containing air and introduce oxygenated air. In the case of submerged fermentation, the oxygenated air may be ambient air supplemented daily through mechanisms including impellers for mechanical agitation of liquid, and air spargers for supplying bubbles of gas to liquid for dissolution of oxygen into the liquid.

The method can further comprise supplementing the cultivation with a carbon source. The carbon source is typically a carbohydrate, such as glucose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, propanol, butanol, pentanol, hexanol, isobutanol, and/or glycerol; fats and oils such as soybean oil, canola oil, rice bran oil, olive oil, corn oil, sesame oil, and/or linseed oil; etc. These carbon sources may be used independently or in a combination of two or more.

In one embodiment, growth factors and trace nutrients for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium. Furthermore, sources of vitamins, essential amino acids, and microelements can be included, for example, in the form of flours or meals, such as corn flour, or in the form of extracts, such as yeast extract, potato extract, beef extract, soybean extract, banana peel extract, and the like, or in purified forms. Amino acids such as, for example, those useful for biosynthesis of proteins, can also be included.

In one embodiment, inorganic salts may also be included. Usable inorganic salts can be potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, lead chloride, copper sulfate, calcium chloride, sodium chloride, calcium carbonate, and/or sodium carbonate. These inorganic salts may be used independently or in a combination of two or more.

In one embodiment, one or more biostimulants may also be included, meaning substances that enhance the rate of growth of a microorganism. Biostimulants may be species-specific or may enhance the rate of growth of a variety of species.

In some embodiments, the method for cultivation may further comprise adding additional acids and/or antimicrobials in the medium before, and/or during the cultivation process. Antimicrobial agents or antibiotics are used for protecting the culture against contamination.

Additionally, antifoaming agents may also be added to prevent the formation and/or accumulation of foam when gas is produced during submerged cultivation.

The pH of the mixture should be suitable for the microorganism of interest. Buffers, and pH regulators, such as carbonates and phosphates, may be used to stabilize pH near a preferred value. When metal ions are present in high concentrations, use of a chelating agent in the medium may be necessary.

The microbes can be grown in planktonic form or as biofilm. In the case of biofilm, the vessel may have within it a substrate upon which the microbes can be grown in a biofilm state. The system may also have, for example, the capacity to apply stimuli (such as shear stress) that encourages and/or improves the biofilm growth characteristics.

In one embodiment, the method for cultivation of microorganisms is carried out at about 5° to about 100° C., preferably, 15 to 60° C., more preferably, 25 to 50° C. In a further embodiment, the cultivation may be carried out continuously at a constant temperature. In another embodiment, the cultivation may be subject to changing temperatures.

In one embodiment, the equipment used in the method and cultivation process is sterile. The cultivation equipment such as the reactor/vessel may be separated from, but connected to, a sterilizing unit, e.g., an autoclave. The cultivation equipment may also have a sterilizing unit that sterilizes in situ before starting the inoculation. Air can be sterilized by methods know in the art. For example, the ambient air can pass through at least one filter before being introduced into the vessel. In other embodiments, the medium may be pasteurized or, optionally, no heat at all added, where the use of low water activity and low pH may be exploited to control undesirable bacterial growth.

In one embodiment, the subject invention further provides a method for producing microbial metabolites such as, for example, biosurfactants, enzymes, proteins, ethanol, lactic acid, beta-glucan, peptides, metabolic intermediates, polyunsaturated fatty acid, and lipids, by cultivating a microbe strain of the subject invention under conditions appropriate for growth and metabolite production; and, optionally, purifying the metabolite. The metabolite content produced by the method can be, for example, at least 20%, 30%, 40%, 50%, 60%, 70%, 80%, or 90%.

The biomass content of the fermentation medium may be, for example, from 5 g/l to 180 g/l or more, or from 10 g/l to 150 g/l. The cell concentration may be, for example, at least $1\times10^9$, $1\times10^{10}$, $1\times10^{11}$, $1\times10^{12}$ or $1\times10^{13}$ cells per gram of final product.

The microbial growth by-product produced by microorganisms of interest may be retained in the microorganisms or secreted into the growth medium. The medium may contain compounds that stabilize the activity of microbial growth by-product.

The method and equipment for cultivation of microorganisms and production of the microbial by-products can be performed in a batch, a quasi-continuous process, or a continuous process.

In one embodiment, all of the microbial cultivation composition is removed upon the completion of the cultivation (e.g., upon, for example, achieving a desired cell density, or density of a specified metabolite). In this batch procedure, an entirely new batch is initiated upon harvesting of the first batch.

In another embodiment, only a portion of the fermentation product is removed at any one time. In this embodiment, biomass with viable cells, spores, conidia, hyphae and/or mycelia remains in the vessel as an inoculant for a new cultivation batch. The composition that is removed can be a cell-free medium or contain cells, spores, or other reproductive propagules, and/or a combination of thereof. In this manner, a quasi-continuous system is created.

Advantageously, the method does not require complicated equipment or high energy consumption. The microorganisms of interest can be cultivated at small or large scale on site and utilized, even being still-mixed with their media.

Preparation of Microbe-Based Products

In some embodiments, the subject invention provides "microbe-based products," which are products to be applied in practice to achieve a desired result. The microbe-based product can be simply a microbe-based composition harvested from the microbe cultivation process. Alternatively, the microbe-based product may comprise further ingredients that have been added. These additional ingredients can include, for example, stabilizers, buffers, carriers (e.g., water or salt solutions), added nutrients to support further microbial growth, non-nutrient growth enhancers and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

One microbe-based product of the subject invention is simply the fermentation medium containing a microorganism of interest and/or the microbial metabolites produced by the microorganism and/or any residual nutrients. The product of fermentation may be used directly without extraction or purification. If desired, extraction and purification can be easily achieved using standard extraction and/or purification methods or techniques described in the literature.

The microorganisms in the microbe-based product may be in an active or inactive form. Furthermore, the microorganisms may be removed from the composition, and the residual culture utilized. The microbe-based products may be used without further stabilization, preservation, and storage. Advantageously, direct usage of these microbe-based products preserves a high viability of the microorganisms, reduces the possibility of contamination from foreign agents and undesirable microorganisms, and maintains the activity of the by-products of microbial growth.

The microbes and/or medium (e.g., broth or solid substrate) resulting from the microbial growth can be removed from the growth vessel and transferred via, for example, piping for immediate use.

In one embodiment, the microbe-based product is simply the growth by-products of the microorganism. For example, biosurfactants produced by a microorganism can be collected from a submerged fermentation vessel in crude form, comprising, for example about 50% pure biosurfactant in liquid broth.

In other embodiments, the microbe-based product (microbes, medium, or microbes and medium) can be placed in containers of appropriate size, taking into consideration, for example, the intended use, the contemplated method of application, the size of the fermentation vessel, and any mode of transportation from microbe growth facility to the location of use. Thus, the containers into which the microbe-based composition is placed may be, for example, from 1 gallon to 1,000 gallons or more. In other embodiments the containers are 2 gallons, 5 gallons, 25 gallons, or larger.

Upon harvesting, for example, the yeast fermentation product, from the growth vessels, further components can be added as the harvested product is placed into containers and/or piped (or otherwise transported for use). The additives can be, for example, buffers, carriers, other microbe-based compositions produced at the same or different facility, viscosity modifiers, preservatives, nutrients for microbe growth, tracking agents, solvents, biocides, other microbes and other ingredients specific for an intended use.

Other suitable additives, which may be contained in the formulations according to the invention, include substances that are customarily used for such preparations. Examples of such additives include surfactants, emulsifying agents, lubricants, buffering agents, solubility controlling agents, pH adjusting agents, preservatives, stabilizers and ultra-violet light resistant agents.

In one embodiment, the product may further comprise buffering agents including organic and amino acids or their salts. Suitable buffers include citrate, gluconate, tartarate, malate, acetate, lactate, oxalate, aspartate, malonate, glucoheptonate, pyruvate, galactarate, glucarate, tartronate, glutamate, glycine, lysine, glutamine, methionine, cysteine, arginine and a mixture thereof. Phosphoric and phosphorous acids or their salts may also be used. Synthetic buffers are suitable to be used but it is preferable to use natural buffers such as organic and amino acids or their salts listed above.

In a further embodiment, pH adjusting agents include potassium hydroxide, ammonium hydroxide, potassium carbonate or bicarbonate, hydrochloric acid, nitric acid, sulfuric acid or a mixture.

In one embodiment, additional components such as an aqueous preparation of a salt, such as sodium bicarbonate or carbonate, sodium sulfate, sodium phosphate, or sodium biphosphate, can be included in the formulation.

Advantageously, in accordance with the subject invention, the microbe-based product may comprise broth in which the microbes were grown. The product may be, for example, at least, by weight, 1%, 5%, 10%, 25%, 50%, 75%, or 100% broth. The amount of biomass in the product, by weight, may be, for example; anywhere from 0% to 100% inclusive of all percentages therebetween.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C. On the other hand, a biosurfactant composition can typically be stored at ambient temperatures.

Local Production of Microbe-Based Products

In certain embodiments of the subject invention, a microbe growth facility produces fresh, high-density microorganisms and/or microbial growth by-products of interest on a desired scale. The microbe growth facility may be located at or near the site of application. The facility produces high-density microbe-based compositions in batch, quasi-continuous, or continuous cultivation.

The microbe growth facilities of the subject invention can be located at the location where the microbe-based product will be used (e.g., a free-range cattle pasture). For example, the microbe growth facility may be less than 300, 250, 200, 150, 100, 75, 50, 25, 15, 10, 5, 3, or 1 mile from the location of use.

Because the microbe-based product can be generated locally, without resort to the microorganism stabilization, preservation, storage and transportation processes of conventional microbial production, a much higher density of microorganisms can be generated, thereby requiring a smaller volume of the microbe-based product for use in the on-site application or which allows much higher density microbial applications where necessary to achieve the desired efficacy. This allows for a scaled-down bioreactor (e.g., smaller fermentation vessel, smaller supplies of starter material, nutrients and pH control agents), which makes the system efficient and can eliminate the need to stabilize cells or separate them from their culture medium. Local generation of the microbe-based product also facilitates the inclusion of the growth medium in the product. The medium can contain agents produced during the fermentation that are particularly well-suited for local use.

Locally-produced high density, robust cultures of microbes are more effective in the field than those that have remained in the supply chain for some time. The microbe-based products of the subject invention are particularly advantageous compared to traditional products wherein cells have been separated from metabolites and nutrients present in the fermentation growth media. Reduced transportation times allow for the production and delivery of fresh batches of microbes and/or their metabolites at the time and volume as required by local demand.

The microbe growth facilities of the subject invention produce fresh, microbe-based compositions, comprising the microbes themselves, microbial metabolites, and/or other components of the medium in which the microbes are grown. If desired, the compositions can have a high density of vegetative cells or propagules, or a mixture of vegetative cells and propagules.

In one embodiment, the microbe growth facility is located on, or near, a site where the microbe-based products will be used (e.g., a livestock production facility), preferably within 300 miles, more preferably within 200 miles, even more preferably within 100 miles. Advantageously, this allows for the compositions to be tailored for use at a specified location. The formula and potency of microbe-based compositions can be customized for specific local conditions at the time of application, such as, for example, which animal species is being treated; what season, climate and/or time of year it is when a composition is being applied; and what mode and/or rate of application is being utilized.

Advantageously, distributed microbe growth facilities provide a solution to the current problem of relying on far-flung industrial-sized producers whose product quality suffers due to upstream processing delays, supply chain bottlenecks, improper storage, and other contingencies that inhibit the timely delivery and application of, for example, a viable, high cell-count product and the associated medium and metabolites in which the cells are originally grown.

Furthermore, by producing a composition locally, the formulation and potency can be adjusted in real time to a specific location and the conditions present at the time of application. This provides advantages over compositions that are pre-made in a central location and have, for example, set ratios and formulations that may not be optimal for a given location.

The microbe growth facilities provide manufacturing versatility by their ability to tailor the microbe-based products to improve synergies with destination geographies. Advantageously, in preferred embodiments, the systems of the subject invention harness the power of naturally-occurring local microorganisms and their metabolic by-products to improve GHG management.

The cultivation time for the individual vessels may be, for example, from 1 to 7 days or longer. The cultivation product can be harvested in any of a number of different ways.

Local production and delivery within, for example, 24 hours of fermentation results in pure, high cell density compositions and substantially lower shipping costs. Given the prospects for rapid advancement in the development of more effective and powerful microbial inoculants, consumers will benefit greatly from this ability to rapidly deliver microbe-based products.

Methods for Reducing Atmospheric Greenhouse Gas Emissions

In preferred embodiments, the subject invention provides a method for reducing emissions of methane, carbon dioxide, and/or other deleterious atmospheric gases, and/or precursors thereof (e.g., nitrogen and ammonia, which are precursors of nitrous oxide), wherein a composition comprising one or more beneficial microorganisms and/or one or more microbial growth by-products is applied to a field or pasture. Preferably, the composition is a multi-purpose composition according to embodiments of the subject invention.

In certain specific embodiments, the livestock animals are ruminants. In a specific embodiment, the field or pasture is a food source for the livestock animals, comprising grasses and/or other plants upon which the livestock animals graze. The livestock animals are placed in the field or pasture to graze to ingest the composition in addition to ingesting the grasses and/or other plants in the pasture.

Advantageously, in preferred embodiments, the methods result in a reduction of methanogenic bacteria and/or protozoa present in the bovine animal's digestive system, particularly, the rumen. In certain embodiments, the methods can also result in a reduction of methane, carbon dioxide, other deleterious atmospheric gases, and/or precursors thereof, such as nitrogen and/or ammonia (precursors of nitrous oxide), in the bovine animal's digestive system and/or waste.

As used herein, "reduction" refers to a negative alteration least 0.25%, 0.5%, 1%, 5%, 10%, 15%, 20%, 25%, 30%, 35%, 40%, 45%, 50%, 55%, 60%, 70%, 75%, 80%, 85%, 90%, 95%, or 100%.

In some embodiments, the desired reduction is achieved within a relatively short time period, for example, within 1 week, 2 weeks, 3 weeks or 4 weeks of the animals ingesting the composition. In some embodiments, the desired reduction is achieved within, for example, 1 month, 2 months, 3 months, 4 months, 5 months or 6 months after employing the subject methods. In some embodiments, the desired reduction is achieved within 1 year, 2 years, 3 years, 4 years, or 5 years after employing the subject methods.

In some embodiments, the methods can further comprise adding materials to enhance the growth of the microorganisms of the subject composition at the time of application (e.g., adding nutrients and/prebiotics). In one embodiment, the nutrient sources can include, for example, sources of magnesium, phosphate, nitrogen, potassium, selenium, calcium, sulfur, iron, copper, zinc, proteins, vitamins and/or carbon. In certain embodiments, the bovine animal can be fed a source of prebiotics, which can include, for example, dry animal fodder, straw, hay, alfalfa, grains, forage, grass, fruits, vegetables, oats, and/or crop residue.

In one embodiment, the prebiotic source can include dry animal fodder, straw, hay, alfalfa, grains, forage, grass, fruits, vegetables, oats, crop residue, humic acid, humate, fulvic acid, and/or kelp extract.

The composition can also be used in combination with other crop management systems, including application of pesticides, herbicides, fertilizers, and/or other soil amendments. In preferred embodiments, the other crop management system is environmentally-friendly and not harmful to humans or livestock.

In some embodiments, prior to applying the composition, the method comprises assessing a livestock animal, field and/or pasture for local conditions, determining a preferred formulation for the composition (e.g., the type, combination and/or ratios of microorganisms and/or growth by-products) that is customized for the local conditions, and producing the composition with said preferred formulation.

The local conditions can include, for example, age, health, size and species of the animal; purpose for producing the animal (e.g., meat, fur, fiber, eggs, labor, milk, etc.); herd size; species within the microbial population of an animal's gut; environmental conditions, such as amount and type of GHG emissions, current climate, and/or season/time of year; species of grasses and/or other plants growing in the field or pasture; mode and/or rate of application of the composition, and others as are deemed relevant.

After assessment, a preferred formulation for the composition can be determined so that the composition can be customized for these local conditions. The composition is then cultivated, preferably at a microbe growth facility that is within 300 miles, preferably within 200 miles, even more preferably within 100 miles of the location of application (e.g., the animal or livestock production facility).

In some embodiments the local conditions are assessed periodically, for example, once annually, biannually, or even monthly. In this way, the composition formula can be modified in real time as necessary to meet the needs of the changing local conditions.

In one embodiment, the composition is applied either as a liquid or a dried product. In one embodiment the composition is broadcast, either in the liquid or dried form, over the field or pasture using, for example, an irrigation system. Additionally, the composition can be applied using a manual spreader, such as a broadcast spreader, a drop spreader, a handheld spreader, or a handheld sprayer.

In an exemplary embodiment, the composition dissolved in water and applied over a field or pasture at 1.0 to 10 fluid oz./acre, or about 1.5 to about 8 fluid oz./acre.

In an exemplary embodiment, the daily dosage of the composition consumed by each animal is about 10 mg to about 10 g, or about 15 mg to about 5 grams, per 100 kg of animal body weight.

In certain embodiments, the methods comprise adding the composition to drinking water and/or feed that is provided to the animals as a supplement to grazing. In some embodiments, the composition is applied to a grazing field or pasture as well as to the drinking water and/or supplemental feed.

In one embodiment, the composition is formulated into the supplemental feed, wherein the composition is added to standard raw food ingredients utilized in producing processed wet and/or dry animal feed.

In some embodiments, the compositions described herein can be co-administered with another feed composition as a dietary supplement. The dietary supplement can have any suitable form such as a gravy, drinking water, beverage, yogurt, powder, granule, paste, suspension, chew, morsel, liquid solution, treat, snack, pellet, pill, capsule, tablet, sachet, or any other suitable delivery form. The dietary supplement can comprise the subject compositions, as well as optional compounds such as vitamins, minerals, probiotics, prebiotics, and antioxidants. In some embodiments, the dietary supplement may be admixed with a feed composition or with water or other diluent prior to administration to the animal.

According to the methods of the subject invention, administration of the compositions can be performed as part of a dietary regimen, which can span a period ranging from parturition through the adult life of the animal. In certain embodiments, the animal is a young or growing animal. In some embodiments, the animal is an aging animal. In other embodiments administration begins, for example, on a regular or extended regular basis, when the animal has reached more than about 30%, 40%, 50%, 60%, or 80% of its projected or anticipated lifespan.

The compositions described herein are administered to an animal via a grazing field or pasture, and optionally, via supplemental feed and/or drinking water, for a time required to accomplish one or more objectives of the invention, such as, a reduction in the amount of methane emissions produced from the animal, without being a detriment to the quality of life, health and wellness of the animal.

In certain embodiments, the methods can also be used for reducing GHG by way of enhanced carbon sequestration, wherein the soil of a field or pasture is inoculated with one or more beneficial microorganisms of the composition, and the beneficial microorganisms promote the growth and health of the plants of the field or pasture.

In one embodiment, the method can be used to inoculate soil and/or a plant's rhizosphere with a beneficial microorganism. The microorganisms of the subject compositions can promote colonization of the roots and/or rhizosphere by beneficial microorganisms, such as, for example, mycorrhizal fungi.

*Mycorrhiza* are fungi that associate symbiotically with plants, wherein the plant makes organic molecules via photosynthesis for the fungus, and the fungus supplies the plant with water and nutrients from the soil. *Mycorrhiza* include endomycorrhizal fungi, which colonize a plant's root tissues intracellulary, and ectomycorrhizal fungi, which colonize the roots extracellularly. *Mycorrhiza* include, for example, *Glomus, Acaulospora, Rhizoctonia, Funneliformis, Endogone, Entrophospora, Gigaspora, Sclerocystis, Scutellospora, Hebeloma, Lactarius* and *Amanila* spp.

In some embodiments, the multi-purpose composition can comprise one or more mycorrhizal fungi, thereby directly inoculating the rhizosphere therewith. In a specific embodiment, a composition comprising *B. amy, Trichoderma harzianum*, and one or more mycorrhizal fungi can produce an improved effect towards enhanced plant biomass and carbon sequestration.

In one embodiment, the promotion of colonization can lead to improved biodiversity of the soil microbiome. As used herein, improving the biodiversity refers to increasing the variety of microbial species within the soil. Preferably, improved biodiversity comprises increasing the ratio of aerobic bacterial species, yeast species, and/or fungal species to anaerobic microorganisms in the soil.

In one embodiment, improved soil biodiversity promotes enhanced nutrient solubilization and/or uptake. For example, certain aerobic bacterial species can acidify the soil and solubilize NPK fertilizers into plant-usable forms.

In one embodiment, the result can be, for example, enhanced vegetative carbon utilization can be in the form of, for example, increased above- and below-ground biomass of plants, including, for example, increased foliage volume, increased stem and/or trunk diameter, enhanced root growth and/or density, and/or increased numbers of plants. In one embodiment, this is achieved by improving the overall hospitability of the rhizosphere in which a plant's roots are growing, for example, by improving the nutrient and/or moisture retention properties of the rhizosphere.

In one embodiment, the result can be, for example, increased soil sequestration in the form of, for example, increased plant root growth, increased uptake by microorganisms of organic compounds secreted by plants (including secretions from plant roots) and improved microbial colonization of soil.

In some embodiments, the methods of the subject invention can be utilized by a livestock producer for reducing carbon credit usage. Thus, in certain embodiments, the subject methods can further comprise conducting measurements to assess the effect of the method on reducing the generation of methane, carbon dioxide and/or other deleterious atmospheric gases, and/or precursors thereof (e.g., nitrogen and/or ammonia); to assess the effect of the method on the control of methanogens and/or protozoa in the livestock animal's digestive system and/or waste; and/or to assess the effect of the method on the sequestration of carbon in the soil of the field or pasture.

These measurements can be conducted according to known methods in the art (see, e.g., Storm et al. 2012, incorporated herein by reference), including, for example, gas capture and quantification, chromatography, respiration chambers (which measure the amount of methane exhaled by an individual animal), and in vitro gas production technique (where feed is fermented under controlled laboratory and microbial conditions to determine amount of methane and/or nitrous oxide is emitted per gram of dry matter). The measurements can also come in the form of testing the microbial population in an animal, for example, by sampling milk, feces, and/or stomach contents and using, for example, DNA sequencing and/or cell plating to determine the number of methanogenic microbes present therein.

Measurements can be conducted at a certain time point after application of the composition. In some embodiments, the measurements are conducted after about 1 week or less, 2 weeks or less, 3 weeks or less, 4 weeks or less, 30 days or less, 60 days or less, 90 days or less, 120 days or less, 180 days or less, and/or 1 year or less.

Furthermore, the measurements can be repeated over time. In some embodiments, the measurements are repeated daily, weekly, monthly, bi-monthly, semi-monthly, semi-annually, and/or annually.

EXAMPLES

A greater understanding of the present invention and of its many advantages may be had from the following examples, given by way of illustration. The following examples are illustrative of some of the methods, applications, embodiments and variants of the present invention. They are not to be considered as limiting the invention. Numerous changes and modifications can be made with respect to the invention.

Example 1—In Vitro Testing

Compositions according to embodiments of the subject invention were screened for their ability to reduce enteric methane and carbon dioxide emissions in cattle. Twenty-four vessels were filled with cattle rumen fluid, artificial saliva, 1 g rumen solids, 1 g super basic ration and 1% by volume of a treatment composition. Triplicates of eight treatments were performed, including one control triplicate. Treatments included:
0—Control
1—B. amy
2—P. ostreatus
3—S. boulardii
4—B. amy+P. ostreatus
5—B. amy+S. boulardii
6—P. ostreatus+S. boulardii
7—B. amy+P. ostreatus+S. boulardii After 24 hours, the amount of methane, carbon dioxide and total gas volumes (ml/gDM) collected from each vessel was measured.

FIG. 1 shows the results for methane. Treatment 1, comprising B. amy, showed a 78% reduction (p=0.05) in average amount of methane gas compared to the control. Treatment 6, comprising S. boulardii and P. ostreatus, showed a 69% reduction (p=0.03) in average amount of methane gas compared to the control.

Figure 2:
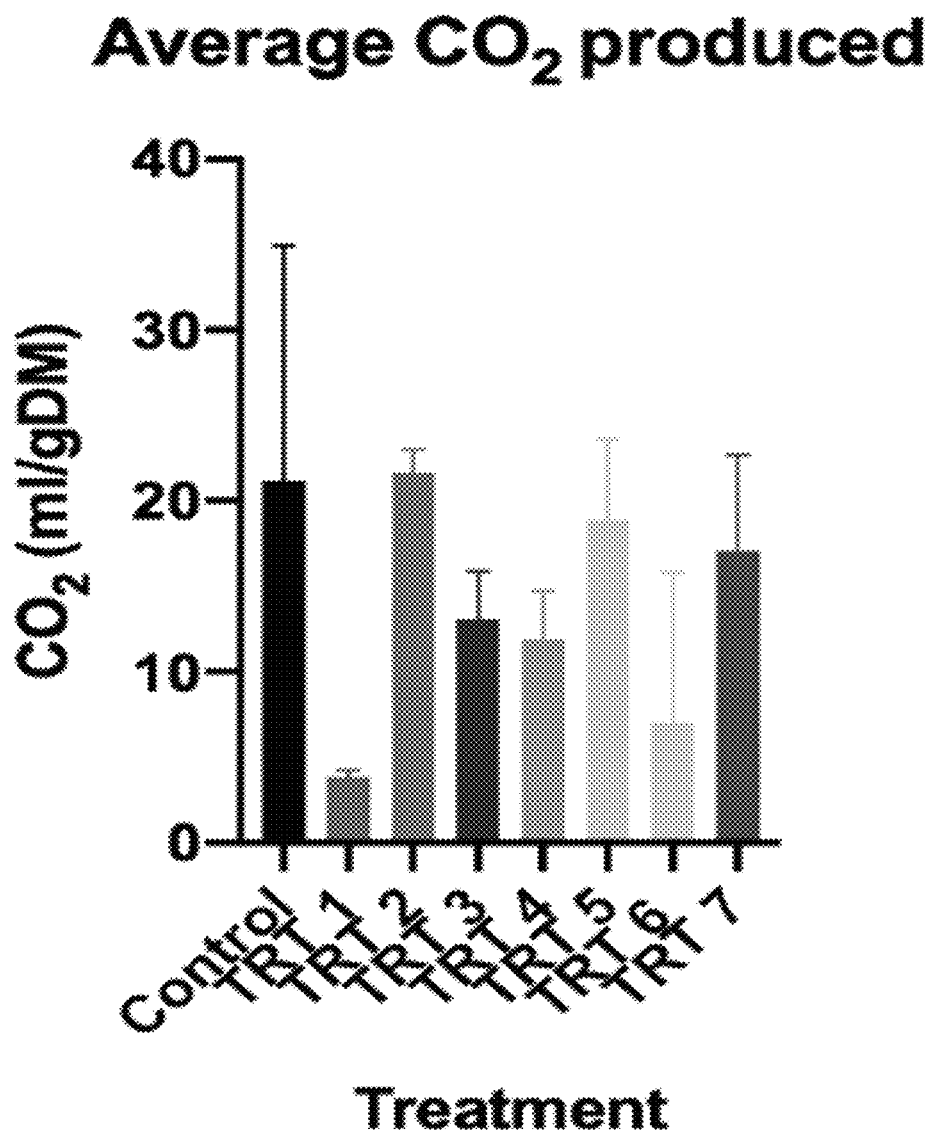
FIG. 2 shows the results of in-vitro studies of compositions according to embodiments of the subject invention to determine their ability to reduce enteric carbon dioxide emissions from cattle rumen. The abbreviation "TRT" is used to refer to "Treatment."

FIG. 2 shows the results for carbon dioxide reduction. Treatment 1, comprising B. amy, showed the greatest reduction in average amount of carbon dioxide gas compared to the control, and Treatment 6, comprising S. boulardii and P. ostreatus, showed the next greatest reduction.

REFERENCES

Government of Western Australia. (2018). "Carbon farming: reducing methane emissions from cattle using feed additives." https://www.agric.wa.gov.au/climate-change/carbon-farming-reducing-methane-emissions-cattle-using-feed-additives. ("Carbon Farming 2018").

Gerber, P. J., et al. (2013). Tackling climate change through livestock—A global assessment of emissions and mitigation opportunities. Food and Agriculture Organization of the United Nations, Rome. Viewed Apr. 5, 2019. http://www.fao.org/3/i3437e/i3437e.pdf. ("Gerber et al. 2013").

Pidwirny, M. (2006). "The Carbon Cycle". Fundamentals of Physical Geography, 2nd Edition. Viewed Oct. 1, 2018. http://www.physicalgeography.net/fundamentals/9r.html. ("Pidwirny 2006").

Storm, Ida M. L. D., A. L. F. Hellwing, N. I. Nielsen, and J. Madsen. (2012). "Methods for Measuring and Estimating Methane Emission from Ruminants." Animals (Basel). June 2(2): 160-183. doi: 10.3390/ani2020160.

United States Environmental Protection Agency. (2016). "Climate Change Indicators in the United States." https://www.epa.gov/sites/production/files/2016-08/documents/climate_indicators_2016.pdf. ("EPA Report 2016").

United States Environmental Protection Agency. (2016). "Overview of Greenhouse Gases." Greenhouse Gas Emissions. https://www.epa.gov/ghgemissions/overview-greenhouse-gases. ("Greenhouse Gas Emissions 2016").

We claim:

1. A method for killing a methanogenic microorganism in a livestock animal's digestive system, the method comprising applying a composition comprising one or more non-genetically-modified beneficial microorganisms and one or more growth by-products thereof to a field or pasture, said field or pasture comprising grasses and/or other plants upon which livestock animals graze, and placing the livestock animals in the field or pasture to graze,
wherein the livestock animals ingest the composition in addition to the grasses and/or other plants, wherein at least one of the one or more beneficial microorganisms is Bacillus amyloliquefaciens NRRL B-67928 at a concentration of about $1\times10^6$ to about $1\times10^{13}$ CFU/ml of the composition, wherein the one or more growth by-products are lipopeptide biosurfactants, and wherein the killing of the methanogenic microorganism reduces enteric deleterious atmospheric gases and/or precursors thereof.

2. The method of claim 1, wherein the livestock animals are ruminants.

3. The method of claim 1, wherein the method further comprises applying an additional microorganism selected from Bacillus subtilis, Pleurotus ostreatus and Saccharomyces boulardii.

4. The method of claim 1, wherein the microbial growth by-products are in crude form, said crude form comprising a supernatant resulting from fermentation of a microorganism that produces said growth by-products.

5. The method of claim 1, further comprising applying a prebiotic with the one or more beneficial microorganisms and/or one or more microbial growth by-products, wherein the prebiotic is dry animal fodder, straw, hay, alfalfa, grains, forage, grass, fruits, vegetables, oats, crop residue, kelp extract, humic acid, fulvic acid, and/or humate.

6. The method of claim 1, further comprising applying one or more of the following components: seaweed; kelp; 3-nitrooxypropanol; anthraquinones; ionophores selected from monensin and lasalocid; polyphenols selected from saponins and tannins; organosulfurs; garlic extract; flavonoids selected from quercetin, rutin, kaempferol, naringin, and anthocyanidins; bioflavonoids isolated from green citrus fruits, rose hips and/or black currants; carboxylic acid; and terpenes selected from d-limonene, pinene and citrus extracts.

7. The method of claim 1, further comprising applying the one or more microorganisms and/or one or more microbial growth by-products to drinking water and/or to supplemental feed that the livestock animals ingest.

8. The method of claim 1, wherein said method enhances plant and microbial biomass in the soil of the field or pasture, thereby producing a carbon sink in the field or pasture.

9. The method of claim 1, wherein the deleterious atmospheric gas is methane or carbon dioxide and/or the deleterious atmospheric gas precursor is nitrogen and/or ammonia.

10. The method of claim 1, further comprising assessing the effect of the method on the reduction of enteric deleterious atmospheric gas emissions and/or precursors thereof in the livestock animal's digestive system and/or waste.

11. The method of claim 1, further comprising assessing the effect of the method on the control of methanogenic bacteria and/or protozoa in the livestock animal's digestive system and/or waste.

12. The method of claim 1, further comprising assessing the effect of the method on the sequestration of carbon in the field or pasture.

13. The method of claim 1, used for reducing the number of carbon credits used by an operator involved in livestock production.

\* \* \* \* \*